United States Patent [19]

Tontarra

[11] Patent Number: 4,751,925
[45] Date of Patent: Jun. 21, 1988

[54] GRIPPER FOR SURGICAL PURPOSES

[76] Inventor: Reinhold Tontarra, Kantstr. 33, 7204 Wurmlingen, Fed. Rep. of Germany

[21] Appl. No.: 814,606

[22] Filed: Dec. 30, 1985

[30] Foreign Application Priority Data

Dec. 28, 1984 [DE] Fed. Rep. of Germany ....... 3447769

[51] Int. Cl.[4] .............................................. A61B 17/00
[52] U.S. Cl. .................................. 128/303 R; 128/305; 128/312; 128/354
[58] Field of Search ............... 128/305, 312, 309, 311, 128/319, 354, 320–325, 303 R

[56] References Cited

U.S. PATENT DOCUMENTS

| 990,882 | 5/1911 | Kratz | 128/305 |
|---|---|---|---|
| 2,381,084 | 8/1945 | Slad | 128/354 |
| 2,733,716 | 2/1956 | Roberts | 128/354 |
| 4,375,218 | 3/1983 | DiGeronimo | 128/354 |
| 4,461,297 | 7/1984 | Sutter | 128/354 |
| 4,569,131 | 2/1986 | Falk et al. | 128/305 |
| 4,590,936 | 5/1986 | Straub et al. | 128/305 |

Primary Examiner—C. Fred Rosenbaum
Assistant Examiner—Gene B. Kartchner

[57] ABSTRACT

A gripper for a surgical attachment has first and second pivotable opposed arms. A spring pretensions the arms in an opening direction. The first arm has a spur and a through-hole. A pin on the second arm has a cap which passes through the through-hole and protrudes from the first arm when the gripper is closed. A link plate is fastened moveably on the first arm, above the through-hole. The plate has a thumb-actuatable projection and a recess to interlock with the pin cap against the force of the spring in the closed position.

13 Claims, 2 Drawing Sheets

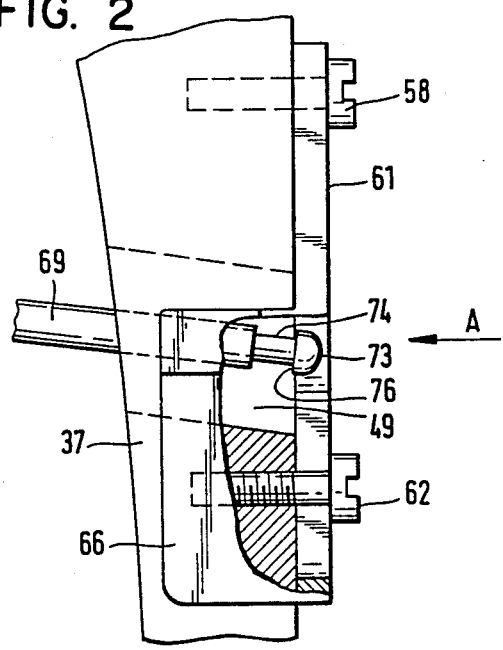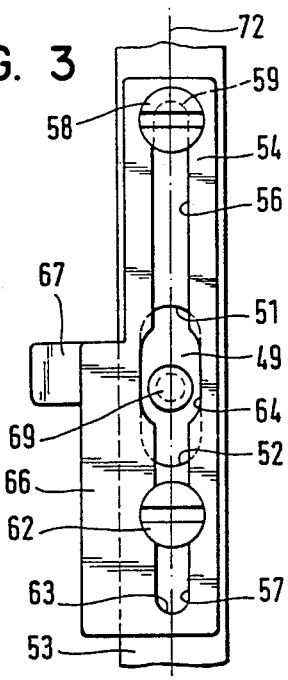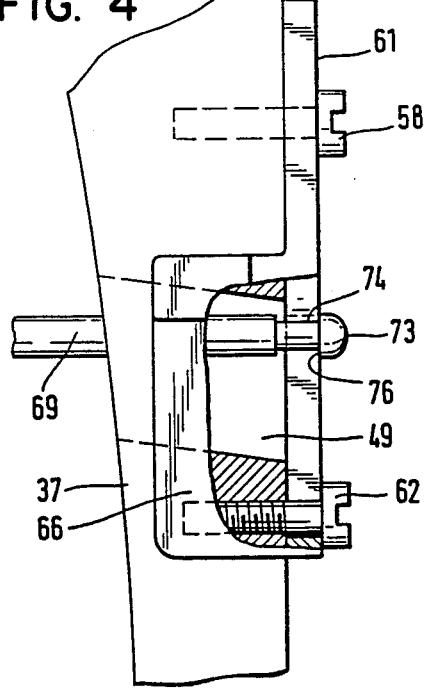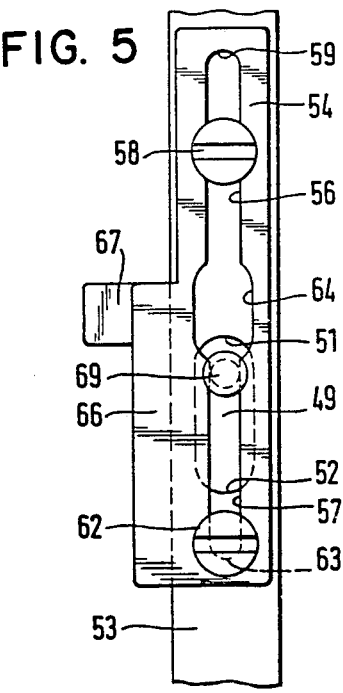

4,751,925

GRIPPER FOR SURGICAL PURPOSES

This invention relates to grippers for surgical attachments, having two rigid double levers pivotable about an axis with respect to each other.

BACKGROUND OF THE INVENTION

Such grippers exist, for example, for intervertebral disk punches, for arthroscoping forceps, for operations in the knee-joint region, for rhinology, for stomach and intestinal surgery. These grippers are used for the actuation of rod-like attachments which are in the range of 1 decimeter or more. The attachments are sometimes interchangeable. At their free end, they bear the actual punching tool, cutting tool or the like.

The attachment has to be inserted through an opening into the inner body. Where there is an opening in the body, it should not be injured during either introduction or withdrawal of the attachment. Injury could arise if, for example, a scissor component, a punch component, a forcep component or the like projects beyond the outline of the attachment.

Up until now, the practice in using such tools has been that the double levers are pushed together by the operating surgeon's hand. In this position, nothing, or very little, projects beyond the outline of the attachment and thus the attachment can be introduced into the opening. Once the tool is in the desired position, it is brought into its initial position by releasing (fully or partially) the arms by the force of the spring action and then cutting, punching or gripping or the like is carried out by renewed pressing together of the arms, overcoming the force of the spring device. When the attachment is withdrawn from the opening, the arms are again pushed together.

This configuration has disadvantages in handling: when introducing the attachment, it is possible that the arms have not been brought completely into closed position and do indeed project a little beyond the outline of the attachment. The same applies in withdrawal of the attachment. It must be imagined here that this introduction and withdrawal could be performed very frequently, for example to take out parts punched-off. If both the arms of the gripper have to be pressed together, namely against the force of the spring device, and the attachment has to be introduced, this makes twin demands both on concentration and on force.

OBJECT AND STATEMENT OF THE INVENTION

The object of the invention is to specify a gripper of the type mentioned at the start which avoids these twin demands in a simple way, permits the operating style used up until now to be retained, permits the grippers likewise to be retained in their basic design, the mode of action of which is immediately obvious to the operating surgeon without lengthy explanation. At the same time, the possibility that the tool can inadvertently assume an intermediate position which is not immediately noticeable is to be excluded.

According to the invention, this object is achieved by the following features:

A first arm on one double lever of the gripper has a portion between a spur and the pivot axis of the double levers having a through-hole which lies parallel to the pivot plane of the lever arms, in a midregion between the spur and the pivot axis. A pin is fastened on a second arm on the other gripper lever, which has a cap area at one end arranged to pass through said through-hole on the first arm. The pin has a length such that the cap area protrudes from the first arm portion when the double levers are pivoted into the closed position of the levers. A link plate is fastened moveably on the first arm portion. The link plate is located above the through-hole and has a thumb actuatable projection. The link plate has a recess arranged and adapted to interlock with the cap area of the pin against the force of the spring device in the closed position of the levers.

Now it is no longer necessary when introducing the attachment to ensure that the arms are fully in closed position and concentration can be focused on introduction or withdrawal of the attachment.

If you wish to allow the arms to be pressed apart by the force of the spring device, release is possible without, for example, having to press out the arms beyond an engagement point, which is accompanied by uncertainty of movement. You do not have to use your other hand, but can work with your thumb which is in any case not really used in this type of operation, and the attachment is hardly tilted when working with the thumb. Advantageously, the invention includes the following additional features:

The through-hole is oval in the longitudinal direction of said first arm portion. By virtue of this feature, the remaining material cross-section of the arm portion is greater than in the case of a circular through-hole.

The through-hole lies a little closer to said pivot axis than to said spur. By this feature, a more suitable overall arrangement of the device according to the invention is achieved. The material cross-section of the arm portion becomes greater and greater towards the axis, so that the material loss due to the through-hole can be tolerated that much more.

It would be possible to make the pin articulated in itself. However, this requires a further joint, and niches with difficult access could occur in sterilization. Furthermore, this would make the gripper more expensive. This is avoided when the pin is fastened rigidly to said second arm, which also makes the pin always have the same position in the link plate.

The through-hole has a size whereby said pin is unimpeded throughout the pivoting movement of said double levers. By this feature, the pin does not bend and, as before, you have a reliable feeling for the two limiting stops of the arms.

The cap area has a mushroom shape with an undercut face. By this feature, on the one hand, you avoid risk of injury on the pin. When the pin is fitted, no particular position need be prescribed with respect to its rotation, and the underside of the mushroom cap can be allowed to interact with the link plate.

The first arm portion has a rear face and said link plate has a platelet which rests on said rear face and an upper side which is aligned in said closed position with said undercut face of said mushroom-shaped cap. By these features, the link plate is fitted at a point which is out of the way and hardly noticeable. The rear face of the arm portion can be used as a guide face and the mushroom cap only appears a little in the closed position, but otherwise disappears entirely.

The upper side of said platelet is in resilient, friction contact against said undercut face of said mushroom-shaped cap, at least when said link plate is moved completely into interlocking position with said cap area. By this feature, the link plate does not move inadvertently.

The resilience friction can be elicited by a minimum bending of the link plate and no separate spring is required.

A device is provided for guiding said platelet linearly on said first arm portion. By this feature, pivot movements of the thumb, which cannot be controlled as well, are avoided and the thumb only need be moved linearly.

The platelet has a longitudinal slot and said guide device comprises two screws having head portions that are wider than said longitudinal slot, which are screwed parallel to each other into said rear face of said first arm portion, said screws extending through said longitudinal slot and resting with their head portions on said upper side of said platelet. By these features, a particularly simple guide device of the platelet in itself and with regard to the cap area of the pin is obtained. A second longitudinal slot is provided in said platelet through which said mushroom-shaped cap passes, which is large enough not to interlock said platelet with said mushroom-shaped cap. By this feature, the mushroom cap can be supported on both its sides in the edge region of the second longitudinal slot.

An angle piece extends at approximately 90 degrees from said platelet and has an inside face which serves as a guide face with respect to said first arm portion. By this feature, a further guide for the platelet and also a resting guide for the tip of the thumb are obtained.

The angle piece has a projection with a non-slip shape, which comprises said thumb-actuated projection on said link plate. By this feature, unintended, and perhaps damaging, movements are avoided due to slipping of the thumb.

DESCRIPTION OF THE DRAWINGS

The invention is now described with reference to a preferred exemplary embodiment. In the drawings.

FIG. 2 shows a broken-off, enlarged side view of a part of FIG. 1, but in closed state of the double levers, in not yet interlocked state.

FIG. 3 shows a view according to the arrow A in FIG. 2 and

FIG. 4 shows a view like FIG. 3, but in the interlocked state of the gripper.

FIG. 1 shows a pair of arthroscoping forceps 11, which have, as essential assemblies, a gripper 12 and an attachment 13. The attachment 13 comprises, in the usual way, a hollow rod 14, in the central bore of which a push-pull rod 16 is provided. At left, the hollow rod 14 merges into a customary knife part 17, ground to be lower, and which interacts with a knife part 18 which is pivotable about a pivot axis 19 by means of the push-pull rod 16. In FIG. 1, the push-pull rod 16 has its full-right position, which corresponds to the open position of the gripper 12. If the push-pull rod 16 moves to the left, the knife part 18 pivots counter clockwise and a piece of tissue located between the knife parts 17, 18 can thus be punched out.

Figure 1:
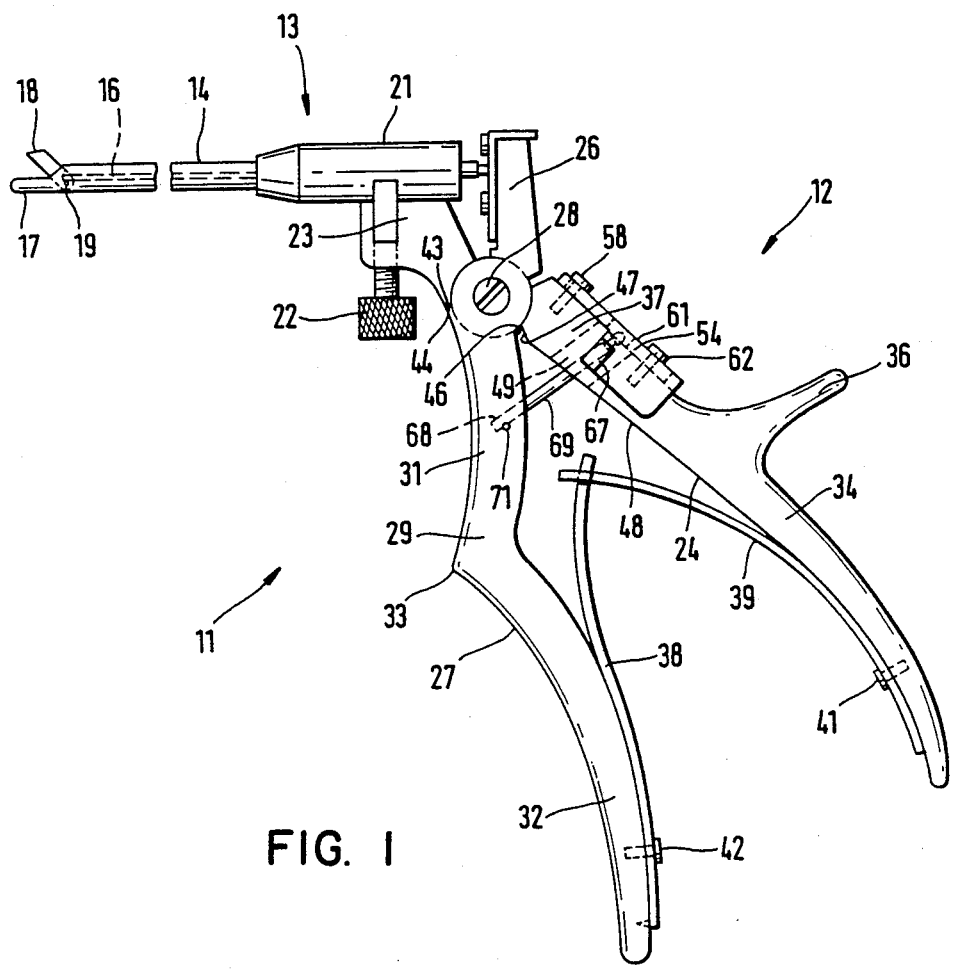
FIG. 1 shows a side view of the gripper with the attachment drawn broken-off, the double levers being in open position.

The hollow rod 14 is held by its right end region in a known way in a mount 21 and is secured against longitudinal movement by a screw 22. The mount 21 is rigidly connected to the upper end region of an arm 23 of a double lever 24, while the end region of the push-pull rod 16 protruding to the right beyond the mount 21 is held in articulated manner by an arm 26 of a double lever 27. The double levers 27 are pivotable about an axis 28. The arms 29 rigidly connected to the arm 26 is divided into two arcs 31, 32, which are shaped such that the index finger lies above the knee 33 and the other fingers lie underneath on the arc 32.

The arm 23 is rigidly connected to an arm 34. Protruding backwards from the latter is a spur 36, which lies opposite the knee 33. During actuation, the ball of the thumb lies on the arm 34 underneath the spur 36. The face 37, directed forwards in FIG. 1, lies opposite the tip of the thumb.

Between the arm 29 and the arm 34 lies a pair of flat springs 38, 39, the lower end region of which is firmly screwed from the inside to the arms 29, 34 by screws 41, 42. The upper end regions of the flat springs 38, 39, prestressed to spread, engage in each other and press the double levers 24, 27 in opening direction. This pivot movement is limited by stops 43, 44, which run radial to the axis 28 and which are provided on the arm 23 or 29, respectively. If the arms 29, 34 are pressed toward each other, the flat springs 38, 39 being pre-tensioned even more, this movement is limited by stops 46, 47, which are provided on the arms 29, 34, radial to the axis 28 and close to the latter, according to the drawing.

In the arm section 48 of the arm 34 lying between the spur 36 and the axis 28, an elongate hole 49 is provided parallel to the plane of the drawing in FIG. 1 and symmetrical in sidewise direction according to the view of FIG. 3, the apexes 51, 52 of which hole run approximately tangential to the axis 28. On the upper side 53 of the arm section 48 is provided a platelet 54, which is of sterilizable metal, has longitudinally rectangular shape and extends virtually over the entire upper side 53 of the arm section 48. The platelet 54 has a front elongate hole 56 and a rear elongate hole 57. Both elongate holes 56, 57 lie centrally in the platelet 54 and align with each other in longitudinal direction. The front elongate hole 56 is crossed by the shank of a cap screw 58, the clear span of the elongate hole 56 corresponding, with slight play, to the diameter of the shank of the cap screw 58. In the state shown in FIG. 3, the apex 59 of the front elongate hole 56 forms a stop at the shank of the cap screw 58. The cap of the cap screw 58 is larger than the clear span of the elongate hole 57, rests, with slight play, in contact on the upper side 61 of the platelet 54, so that the platelet 54 is longitudinally guided while held down there.

On the other side of the elongate hole 49, a second cap screw 62 is screwed in parallel to the first cap screw 58 and crosses the rear elongate hole 57 with its shank. The guide function is analagous to that described above and also corresponds to the configuration. Here an apex 63 forms the stop. The stop of the apexes 59, 63 is longer, by the travel necessary for the platelet 54, than the distance between the shanks of the cap screws 58, 62.

The front elongate hole 58 and the rear elongate hole 57 merge into each other because they both open out into a substantially shorter passage hole 64, which is arranged substantially above the elongate hole 49.

When held in the right hand, the platelet 54 merges to the left into an angle piece 66, which lies at 90° to the platelet 54, is about half as long as the platelet 54 and is arranged in the lower region of the latter according to FIG. 4. The angle piece 66 has a slight play with the face 37, is approximately rectangular and is provided where the tip of the thumb normally lies when working with the gripper 12. In its region facing the axis 28, the angle piece 66 merges into a projection 67 which is only 2.5 mm high and can be used by the thumb to guide the platelet 54, according to FIG. 3, upward or back into the position drawn. On account of the play and even with spring effects occurring, the force on the projection 67 necessary for actuation is always quite substantially less than the maximum force which can be applied by the thumb of an adult. The projection 67 lies approximately on a level with the elongate hole 49, even in its two end positions. The total travel is about 5 mm.

Approximately tangential to the axis 28, a blind hole 68 is drilled centrally into the arc 31 from its rear side, in which hole the front region of a straight pin 69, of about 2.5 mm in diameter, is inserted. It is secured by a cross peg 71. In the open state of the gripper 12 according to FIG. 1, the straight pin 69 protrudes through the elongate hole 49 into the passage hole 64, which has a substantially larger clear span than the straight pin 69 lying symmetrically in it. FIGS. 3 and 4 show that the mid axis of the straight pin 69 is in the geometrical longitudinal plane 72 which is also the plane of symmetry for the shanks of the cap screws 58, 62, of the front elongate hole 56, of the rear elongate hole 57, of the passage hole 64 and of the arm 34. The end face of the straight pin 69 is formed by a dome 73. According to FIG. 2, on the left of the dome a circular-cylindrical constriction 74 is provided in the straight pin 69, which constriction is somewhat longer than the platelet 54 is thick and whose annular end face 76 on the right according to FIG. 1 lies in just such a position that, with the gripper 12 closed, the end face 76 rests with pre-tension and friction in contact with the upper side 61 in the upper region of the rear elongate hole 57 according to FIG. 3, as shown in FIG. 4. Then the knife part 18 is in its counter clockwise pivoted position and crosses partially with the knife part 17. In this position, the hollow rod 14 can be introduced atraumatically into an opening.

The interlock device described operates favorably to this extent: the apex 63 can be pushed only up to the stop against the shank of the cap screw 62. This results in the end face 76 sliding only a short, but adequate, stretch on the upper side. In this process, the thumb must exert more than just the displacement force as some energy is required, on account of the chosen flank of ascent between the end face 76 and the shape of the upper side 61 in the region of the transition from the through-hole 64 to the rear elongate hole 57, which also pretensions the platelet 54 to a slight flexure.

Upon release of the interlock, the tip of the thumb fetches the projection 67. This is not a precision operation because the through-hole 64 is, after all, substantially longer than the diameter of the straight pin 69.

Thus, the operating surgeon does not have to use delicate manipulation here.

The gripper 12 is made of the usual metal for such objects and thus is also somewhat resilient. Although the stops 46, 47 are in contact with each other, the arms 23, 29 can be resiliently pressed further against each other, so that the end face 76 lifts off the upper side 61. Thus, in locking, the spring force of the arms 23, 26 and/or of the flat springs 38, 29 can be relied upon.

I claim:

1. A gripper for a surgical attachment, comprising two rigid double levers directly coupled with said attachment and pivotable about a pit axis with respect to each other, having a pair of first and second opposed shorter arms and a pair of first and second opposed longer arms extending from said pivot axis, said arms being pivotable in a pivot plane through an angle of less than 30 degrees in a direction towards an open position and a direction towards a closed position of said double levers, said first longer arm having a rear face thereon facing in the direction away from said second longer arm, a spring device between said longer arms which is arranged to pretension said arms in the opening direction, a single first stop, separate from said attachment, for limiting the movement of said double levers in said opening direction, a second stop, separate from said attachment for stopping movement of said double levers at said closed position, a spur on said rear face on said first longer arm facing in the direction away from said second longer arm, said spur extending in said pivot plane, said first longer arm having a portion between said spur and said pivot axis having a through-hole which lies parallel to said pivot plane in a mid-region between said spur and said pivot axis and opens to said rear face, said second stop comprising a pin fastened on said second longer arm, which has a cap area at one end, extending in said pivot plane and arranged to pass through said through-hole, said pin having a length such that said cap area protrudes from said rear face of said first longer arm portion when said double levers are pivoted into said closed position, and a link plate resting on said rear face and fastened movably in a longitudinal direction on said first longer arm portion, said link plate being located above said through-hole and having a thumb-actuable projection thereon and extending to the side thereof, said link plate having a recess arranged and adapted to interlock with said cap area of said pin against the force of said spring device in said closed position.

2. A gripper as claimed in claim 1, wherein said through-hole is oval in the longitudinal direction of said first arm portion.

3. A gripper as claimed in claim 1, wherein said through-hole lies a little closer to said pivot axis than to said spur.

4. A gripper as claimed in claim 1, wherein said pin is fastened rigidly to said second arm.

5. A gripper as claimed in claim 1, wherein said through-hole has a size whereby said pin is unimpeded throughout the pivoting movement of said double levers.

6. A gripper as claimed in claim 1, wherein said cap area has a mushroom shape with an undercut face.

7. A gripper as claimed in claim 6, wherein said first arm portion has a rear face and said link plate has a platelet which rests on said rear face and an upper side which is aligned in said closed position with said undercut face of said mushroom-shaped cap.

8. A gripper as claimed in claim 7, wherein said upper side of said platelet is in resilient, friction contact against said undercut face of said mushroom-shaped cap, at least when said link plate is moved completely into interlocking position with said cap area.

9. A gripper as claimed in claim 7, comprising a device for guiding said platelet linearly on said first arm portion.

10. A gripper as claimed in claim 9, wherein said platelet has a longitudinal slot and said guide device comprises two screws having head portions that are wider than said longitudinal slot, which are screwed parallel to each other into said rear face of said first arm portion, said screws extending through said longitudinal slot and resting with their head portions on said upper side of said platelet.

11. A gripper as claimed in claim 8, comprising a second longitudinal slot in said platelet through which said mushroom-shaped cap passes, which is large enough not to interlock said platelet with said mushroom-shaped cap.

12. A gripper as claimed in claim 7, comprising an angle piece extending at approximately 90 degrees from said platelet and having an inside face which serves as a guide face with respect to said first arm portion.

13. A gripper as claimed in claim 12, wherein said angle piece has a projection with a non-slip shape, which comprises said thumb-actuated projection on said link plate.

* * * * *